US012790324B2

(12) United States Patent
Palle et al.

(10) Patent No.: US 12,790,324 B2
(45) Date of Patent: Nov. 10, 2026

(54) CRYSTALLINE FORM OF ISAVUCONAZONIUM SULFATE AND A PROCESS FOR ITS PREPARATION

(71) Applicant: Alivus Life Sciences Limited, Solapur (IN)

(72) Inventors: Venkata Raghavendra Acharyulu Palle, Pune (IN); Suresh Kadam, Thane (IN); Sukumar Sinha, Navi Mumbai (IN); Sachin Gavhane, Thane (IN); Sandeep Khandgale, Kalyan (IN); Anil Bhujbal, Dombivli (IN); Jayant Patil, Nasik (IN)

(73) Assignee: Alivus Life Sciences Limited, Solapur (IN)

( * ) Notice: Subject to any disclaimer, the term of this patent is extended or adjusted under 35 U.S.C. 154(b) by 195 days.

(21) Appl. No.: 18/835,939

(22) PCT Filed: Nov. 21, 2022

(86) PCT No.: PCT/IB2022/061207
§ 371 (c)(1),
(2) Date: Aug. 5, 2024

(87) PCT Pub. No.: WO2023/148544
PCT Pub. Date: Aug. 10, 2023

(65) Prior Publication Data

US 2025/0145610 A1 May 8, 2025

(30) Foreign Application Priority Data

Feb. 4, 2022 (IN) ............................ 202221006158

(51) Int. Cl.

| | |
|---|---|
| ***C07D 417/14*** | (2006.01) |
| ***A61K 31/4439*** | (2006.01) |
| ***A61P 31/10*** | (2006.01) |

(52) U.S. Cl.
CPC ........ *C07D 417/14* (2013.01); *A61K 31/4439* (2013.01); *A61P 31/10* (2018.01); *C07B 2200/13* (2013.01)

(58) Field of Classification Search
None
See application file for complete search history.

(56) References Cited

FOREIGN PATENT DOCUMENTS

| | | | |
|---|---|---|---|
| CN | 106565699 B * | 7/2019 | .......... C07D 417/14 |
| IN | 201621035182 A | 10/2019 | |

(Continued)

OTHER PUBLICATIONS

Wu, Shuming, et al. "Review of the Patent and Journal Literature: Synthesis and Final Forms of Antifungal Prodrug Isavuconazonium Sulfate." Organic Process Research & Development, vol. 29, No. 7, Jul. 2025, pp. 1635-1653. DOI.org (Crossref), https://doi.org/10.1021/acs.oprd.5c00129. (Year: 2025).*

(Continued)

*Primary Examiner* — Clinton A Brooks
*Assistant Examiner* — Kyle Nottingham
(74) *Attorney, Agent, or Firm* — Michael E. Carmen

(57) ABSTRACT

The present invention relates to a crystalline form of isavuconazonium sulfate. The present invention also relates to a process for preparation of isavuconazonium sulfate and a pharmaceutical composition containing the crystalline isavuconazonium sulfate. The invention also relates to a method for the treatment of fungal infections such as invasive aspergillosis and mucormycosis comprising administering a therapeutically effective amount of crystalline isavuconazonium sulfate to a subject in need thereof. The invention also provides isavuconazonium sulfate having high purity.

15 Claims, 3 Drawing Sheets

(56) References Cited

FOREIGN PATENT DOCUMENTS

| | | | | | |
|---|---|---|---|---|---|
| IN | 201821035971 | A | | 3/2020 | |
| WO | 2020025553 | A1 | | 2/2020 | |
| WO | WO-2023238014 | A1 | * | 12/2023 | ........... C07D 417/14 |

OTHER PUBLICATIONS

Cruz-Cabeza, Aurora J., et al. "Open Questions in Organic Crystal Polymorphism." Communications Chemistry, vol. 3, No. 1, Oct. 2020, p. 142. www.nature.com, https://doi.org/10.1038/s42004-020-00388-9. (Year: 2020).*

International Search Report, PCT/IB2022/061207 dated Feb. 13, 2023.

M.R. Caira, "Crystalline polymorphism of organic compounds", Topics in Current Chemistry, Springer, Berlin, DE, Jan. 1, 1998, pp. 163-208, vol. 198.

* cited by examiner

CRYSTALLINE FORM OF ISAVUCONAZONIUM SULFATE AND A PROCESS FOR ITS PREPARATION

PRIORITY

This application claims priority under 35 U.S.C. § 371 to International Application No. PCT/IB2022/061207, filed Nov. 21, 2022, which claims the benefit of Indian Provisional Application No. 202221006158, entitled "Process for preparation of isavuconazonium sulfate," filed Feb. 4, 2022, the contents of each of which are incorporated herein by reference.

FIELD OF THE INVENTION

The present invention relates to a crystalline form of isavuconazonium sulfate, a process for its preparation, and a pharmaceutical composition containing the crystalline isavuconazonium sulfate. The invention also relates to a method for the treatment of fungal infections such as invasive aspergillosis and mucormycosis comprising administering a therapeutically effective amount of crystalline isavuconazonium sulfate to a subject in need thereof. The invention also provides isavuconazonium sulfate having high purity.

BACKGROUND OF THE INVENTION

Isavuconazonium sulfate is a prodrug of isavuconazole, an azole antifungal drug. The chemical name of isavuconazonium sulfate is (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy)carbonyl](methyl) amino}pyridin-3-yl)methyl-N-methylglycinate monosulfate, which is set forth herein below as a compound of formula I.

Isavuconazonium sulfate (CRESEMBA®) is approved by the U.S. FDA (the U.S. Food and Drug Administration) in 2015 for use in the treatment of invasive aspergillosis and mucormycosis, which infections are seen predominantly in immunocompromised patients, and are life-threatening fungal infections.

Isavuconazonium sulfate marketed as CRESEMBA® is a capsule for oral administration. Isavuconazonium sulfate is also marketed as CRESEMBA® for injection for intravenous administration.

In light of the efficacy of isavuconazonium sulfate, and the known fact that different solid forms of active pharmaceutical substances provide numerous advantages, such as improved solubility, dissolution profile, better stability, shelf-life etc., there exists a need to provide novel crystalline form of isavuconazonium sulfate having beneficial properties.

Moreover, it is also a known fact that providing drug substances having high purity is considered a critical aspect in pharmaceutical industry, particularly for ensuring the safety, efficacy and consistency of the pharmaceutical composition containing the active pharmaceutical ingredient (API).

In view of the importance of providing drug substances in high purity, better storage stability, and ease of preparing finished dosage form, an object of the present invention is to provide a novel crystalline form of isavuconazonium sulfate; a process for the preparation of the crystalline isavuconazonium sulfate; a pharmaceutical composition comprising the crystalline isavuconazonium sulfate; and use of the crystalline isavuconazonium sulfate in the treatment of life threatening fungal infections.

SUMMARY OF THE INVENTION

The present invention provides a novel crystalline form of isavuconazonium sulfate represented by the compound of formula I set forth below, and designated as Form GL-1 (hereinafter referred to as "crystalline Isavuconazonium sulfate" or "Form GL-1"), characterized by data selected from the group consisting of: an X-ray powder diffraction (XRPD) pattern having peaks at 6.45, 7.25, 15.98, 16.87, 17.25 and 20.93±0.2 degrees 2-theta; an XRPD pattern substantially as depicted in FIG. 1; an IR (infra-red) spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±2 $cm^{-1}$; an IR spectrum as depicted in FIG. 2; and a thermogravimetric Analysis (TGA) thermogram showing a weight loss of about 6.56% up to 150° C. determined over the temperature range of 0° C. to 250° C., and heating rate of 10° C./min; an TGA thermogram substantially as depicted in FIG. 3 and combinations thereof.

The present invention further provides crystalline isavuconazonium sulfate (Form GL-1) characterized by an XRPD pattern having one or more additional peaks at 12.5, 17.83, 21.99 and 22.56±0.2 degrees 2-theta.

The present invention also provides a process for the preparation of isavuconazonium sulfate, a compound of formula I, represented by the following structure:

I

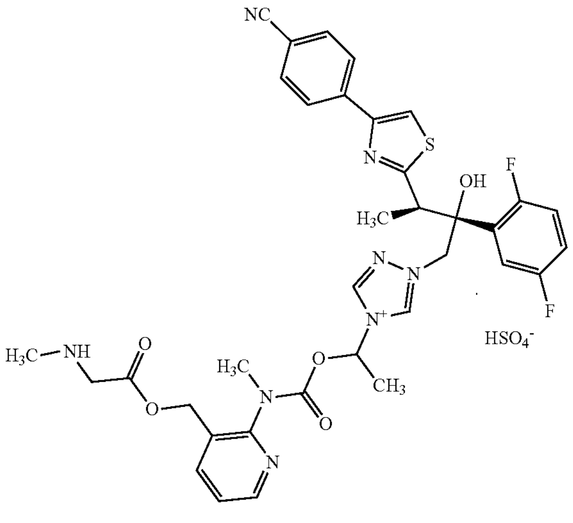

comprising:

(a) providing a reaction mixture comprising isavuconazonium sulfate and a solvent system comprising a nitrile solvent and water;

(b) stirring the reaction mixture of step (a) to precipitate isavuconazonium sulfate; and (c) isolating isavuconazonium sulfate as obtained in step (b); wherein the isolated isavuconazonium sulfate is in the crystalline form designated as crystalline isavuconazonium sulfate (Form GL-1).

The present invention also provides a pharmaceutical composition comprising a therapeutically effective amount of the above described crystalline isavuconazonium sulfate, and at least one pharmaceutically acceptable excipient.

The present invention further provides a method for the treatment of fungal infections which comprises administering a therapeutically effective amount of crystalline isavuconazonium sulfate to a subject in need thereof.

DETAILED DESCRIPTION OF THE INVENTION

Various illustrative embodiments described herein are directed to a novel crystalline form of isavuconazonium sulfate, a compound of formula I and designated as Form GL-1 (the "crystalline isavuconazonium sulfate" or "Form GL-1"), represented by the following structure:

I

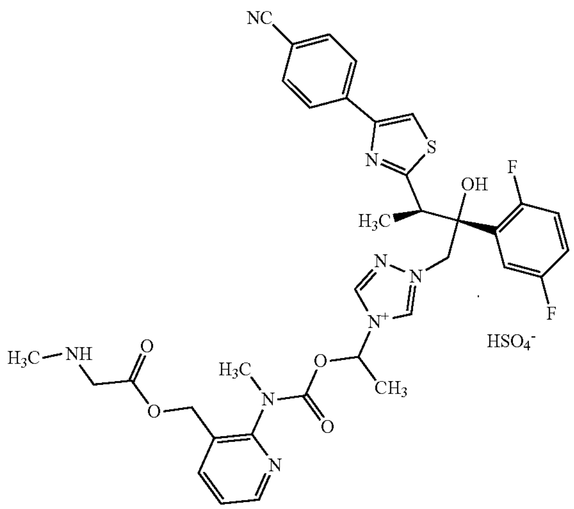

Crystalline isavuconazonium sulfate (Form GL-1) of the present invention can be characterised by different analytical parameters, alone or in combination such as, but not limited to, X-ray powder diffraction (XRPD) pattern peaks at 2-theta values; IR spectrum; Thermogravimetric Analysis (TGA) thermogram, and/or any other method of characterization of a solid state form such as solid state, $^{13}C$ NMR spectrum; and Raman spectrum that are known to a person skilled in the art.

In an embodiment, the present invention provides crystalline isavuconazonium sulfate characterized by an XRPD pattern having peaks at 6.45, 7.25, 15.98, 16.87, 17.25 and 20.93±0.2 degrees 2-theta.

In one or more additional embodiments, as may be combined with the preceding paragraphs, the present invention provides crystalline isavuconazonium sulfate characterized by XRPD pattern having one or more additional peaks at 12.5, 17.83, 21.99 and 22.56±0.2 degrees 2-theta.

In an additional embodiment, crystalline isavuconazonium sulfate of the present invention may alternatively be characterized by an XRPD pattern having peaks at 6.45, 7.25, 12.5, 15.98, 16.87, 17.25, 17.83, 20.93, 21.99 and 22.56±0.2 degrees 2-theta.

In an additional embodiment, crystalline isavuconazonium sulfate of the present invention may be characterized by XRPD pattern having at least four peaks at 6.45, 7.25, 12.5, 15.98, 16.87, 17.25, 17.83, 20.93, 21.99 and 22.56±0.2 degrees 2-theta.

Figure 1:
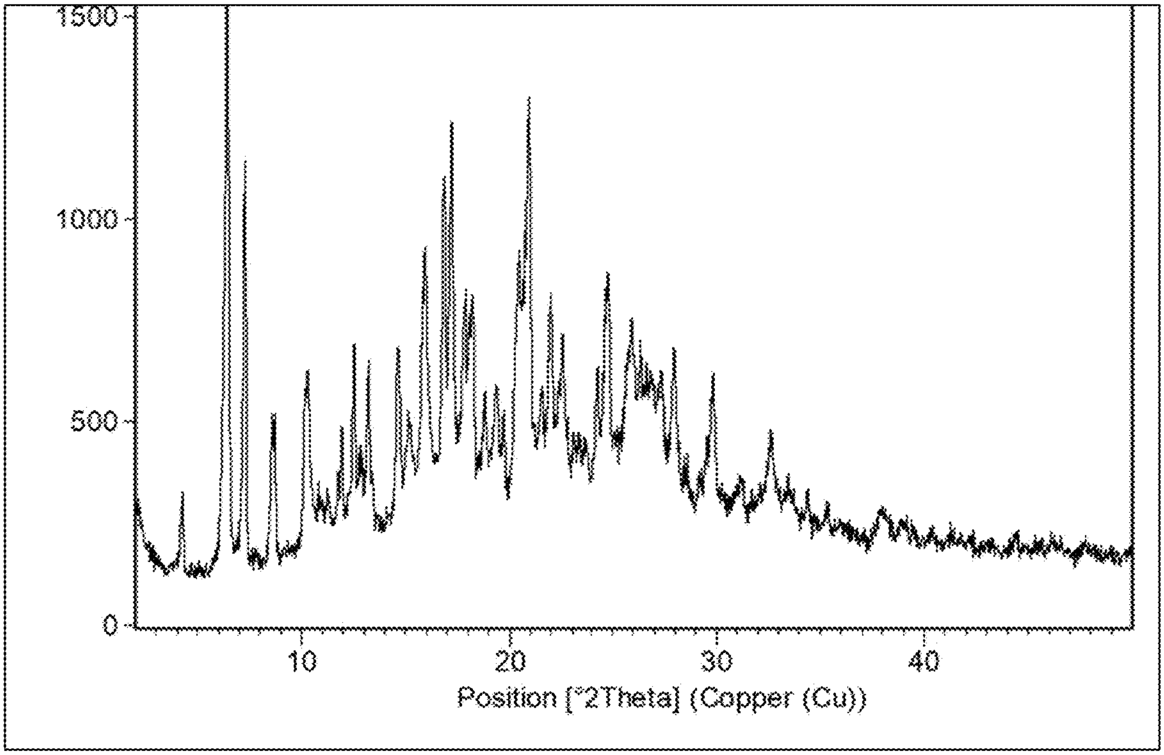
FIG. 1 depicts a characteristic X-ray powder diffraction (XRPD) pattern of crystalline isavuconazonium sulfate (Form GL-1).

In an embodiment, as may be combined with the preceding paragraphs, the present invention provides crystalline isavuconazonium sulfate characterised by an XRPD pattern substantially as shown in FIG. 1.

In an embodiment, the present invention provides crystalline isavuconazonium sulfate characterised by an XRPD pattern substantially as shown in FIG. 1.

The phrase "XRPD pattern substantially as shown in FIG. 1" means that for comparison purposes some variability in peak intensities from those shown in FIG. 1 is allowed. It will be understood by a person skilled in the art that the 2-theta values of the XRPD pattern for the crystalline isavuconazonium sulfate of the present invention may vary slightly from one instrument to another and also depending on variations in sample preparation and batch to batch variation. Therefore, the 2 theta values are not to be construed as absolute. Person skilled in the art will also understand that the relative intensities of peaks may vary depending on orientation effects.

In an embodiment, the present invention provides crystalline isavuconazonium sulfate (Form GL-1) characterised by IR spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±2 $cm^{-1}$.

Figure 2:
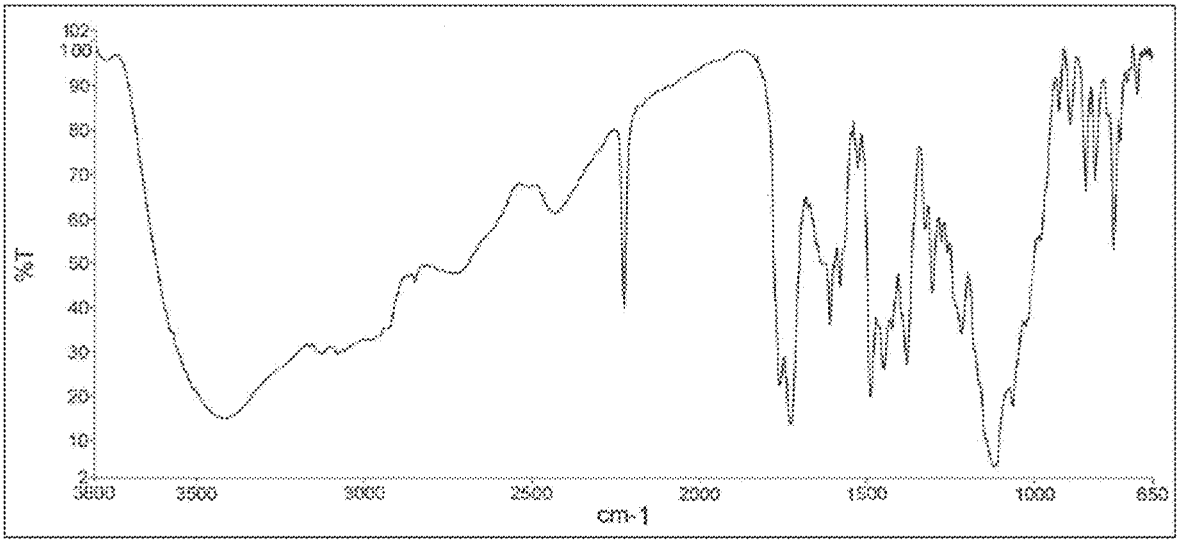
FIG. 2 depicts a characteristic Infra-Red (IR) spectrum of crystalline isavuconazonium sulfate (Form GL-1).

In an embodiment, as may be combined with the preceding paragraphs, the present invention provides crystalline isavuconazonium sulfate (Form GL-1) characterised by IR spectrum as shown in FIG. 2.

In an embodiment, the present invention provides crystalline isavuconazonium sulfate characterised by an IR spectrum as shown in FIG. 2.

In an embodiment, the present invention provides crystalline isavuconazonium sulfate (Form GL-1) characterized by thermogravimetric analysis (TGA) thermogram, showing a weight loss of about 6.56% up to 150° C. determined over the temperature range of 0° C. to 250° C., and heating rate of 10° C./min.

Figure 3:
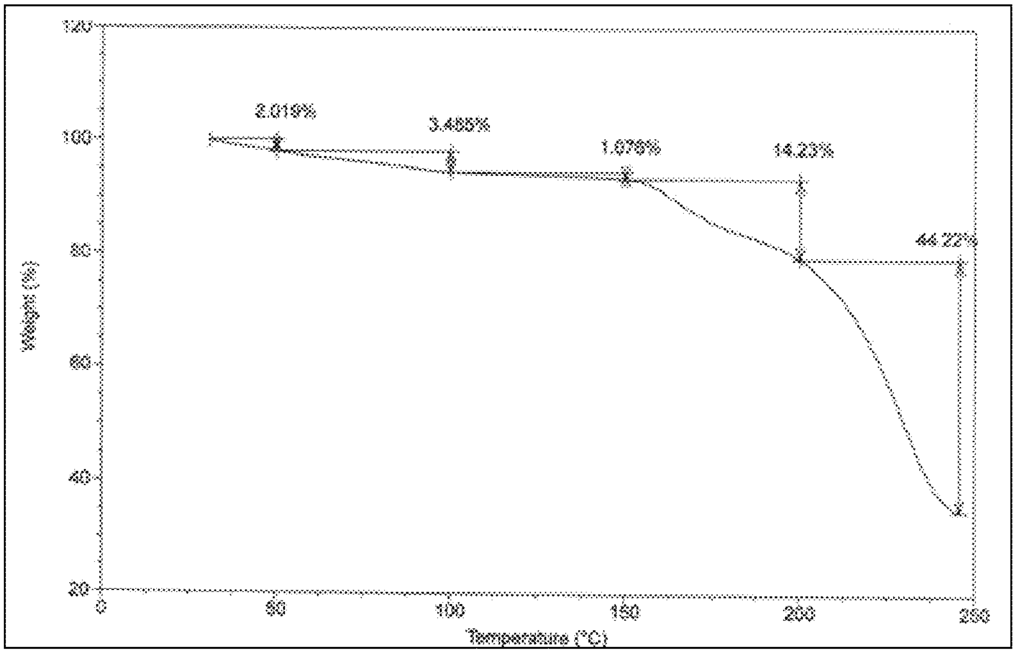
FIG. 3 depicts a characteristic Thermogravimetric Analysis (TGA) thermogram of crystalline isavuconazonium sulfate (Form GL-1).

In an embodiment, as may be combined with the preceding paragraphs, the present invention provides crystalline isavuconazonium sulfate (Form GL-1) characterised by TGA thermogram substantially as shown in FIG. 3.

In an embodiment, the present invention provides crystalline isavuconazonium sulfate characterised by TGA thermogram substantially as shown in FIG. 3.

The phrase "substantially as shown in FIG. 3" means that the reported TGA features can vary by about ±5° C.

In an embodiment, the present invention provides crystalline isavuconazonium sulfate (Form GL-1) characterised by one or more data selected from the group consisting of: an XRPD pattern having peaks at 6.45, 7.25, 15.98, 16.87, 17.25 and 20.93±0.2 degrees 2-theta; an IR spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±2 $cm^{-1}$; and a thermogravimetric Analysis (TGA) thermogram, showing a weight loss of about 6.56% up to 150° C. determined over the temperature range of 0° C. to 250° C., and heating rate of 10° C./min.

In an embodiment, the present invention provides crystalline isavuconazonium sulfate (Form GL-1) having at least 30% crystallinity.

In an embodiment, the present invention provides crystalline isavuconazonium sulfate (Form GL-1) wherein the amorphous content of isavuconazonium sulfate is 70% or less.

In an embodiment, the present invention provides crystalline isavuconazonium sulfate (Form GL-1) wherein the amorphous content of isavuconazonium sulfate is 65% or less.

In an embodiment, the present invention provides a composition comprising crystalline isavuconazonium sulfate (Form GL-1), wherein the amorphous content of isavuconazonium sulfate is 70% or less.

In an embodiment, the present invention also provides a process for the preparation of isavuconazonium sulfate, a compound of formula I,

I

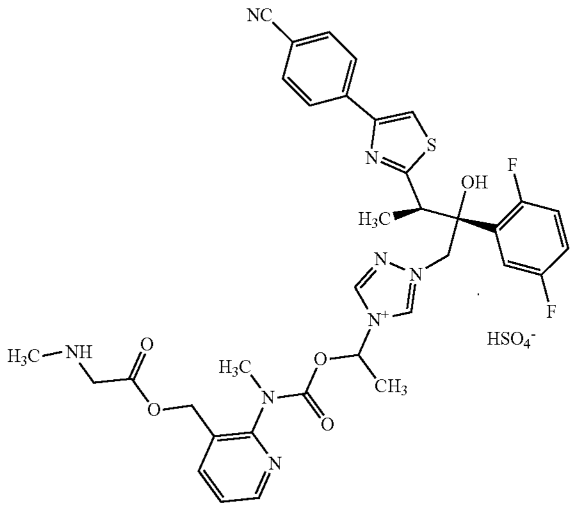

comprising:

(a) providing a reaction mixture comprising isavuconazonium sulfate and a solvent system comprising a nitrile solvent and water;

(b) stirring the reaction mixture of step (a) to precipitate isavuconazonium sulfate; and (c) isolating isavuconazonium sulfate as obtained in step (b), wherein the isolated isavuconazonium sulfate is in crystalline form (the "crystalline isavuconazonium sulfate").

In an embodiment, in step (a) of the above process, the reaction mixture may be obtained by the addition of isavuconazonium sulphate to a solvent system comprising a mixture of a nitrile solvent and water.

In another embodiment, in step (a) of the above process, the reaction mixture may be obtained by the addition of a solvent system comprising a nitrile solvent and water to isavuconazonium sulfate.

In an embodiment, the nitrile solvent is selected from the group consisting of acetonitrile, propionitrile and isobutyronitrile.

In an embodiment, the addition of isavuconazonium sulfate to the solvent system comprising a nitrile solvent and water, or the addition of the solvent system comprising a nitrile solvent and water to isavuconazonium sulfate may be carried out at a temperature of about 0° C. to about 25° C.

The term "about" as used herein, refers to a value which lies within the range defined by a variation of up to ±10% of the value, preferably up to ±5% of the value.

The addition of isavuconazonium sulfate to the solvent system, or the addition of the solvent system to isavuconazonium sulfate may be carried out over a period of about 10 minutes to about 1 hour.

In an embodiment, in step (b), the reaction mixture of step (a) comprising isavuconazonium sulfate and a solvent system comprising a nitrile solvent and water may be stirred for a period of about 1 hour to about 24 hours.

In one embodiment, the reaction mixture of step (a) may be stirred for a period of about 3 hours to about 15 hours.

The reaction mixture comprising isavuconazonium sulfate and a solvent system comprising a nitrile solvent and water may be stirred at a temperature of about 0° C. to about 35° C.

In an embodiment, the reaction mixture comprising isavuconazonium sulfate and a solvent system comprising a nitrile solvent and water may be stirred at a temperature of about 10° C. to about 30° C.

In an embodiment, the reaction mixture comprising isavuconazonium sulfate and a solvent system comprising of a nitrile solvent and water may be stirred for a period of about 1 hour to 24 hours at a temperature of about 0° C. to about 35° C. to precipitate isavuconazonium sulfate.

In an embodiment, in step (c) of the above process, the isavuconazonium sulfate obtained in step (b) is isolated by methods such as, for example, filtration, centrifugation, etc.

In an embodiment, the present invention provides a process for the preparation of crystalline isavuconazonium sulfate (Form GL-1) comprising:

(a) providing a reaction mixture comprising isavuconazonium sulfate and a solvent system comprising a nitrile solvent and water;

(b) stirring the reaction mixture of step (a) to precipitate isavuconazonium sulfate; and (c) isolating isavuconazonium sulfate as obtained in step (b), wherein the isolated isavuconazonium sulfate is in crystalline form, the crystalline isavuconazonium sulfate (Form GL-1), which is characterised by one or more data selected from the group consisting of: an XRPD pattern having peaks at 6.45, 7.25, 15.98, 16.87, 17.25 and 20.93±0.2 degrees 2-theta; an IR spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±2 $cm^{-1}$; and a thermogravimetric Analysis (TGA) thermogram, showing a weight loss of about 6.56% up to 150° C. determined over the temperature range of 0° C. to 250° C., and heating rate of 10° C./min.

In an embodiment, the present invention provides a process using the foregoing steps (a)-(c) for the preparation of crystalline isavuconazonium sulfate (Form GL-1); wherein the crystalline form is further characterized by XRPD pattern having one or more additional peaks at 12.5, 17.83, 21.99 and 22.56±0.2 degrees 2-theta.

In an embodiment, the nitrile solvent used in step (a) of the process for the preparation of crystalline isavuconazonium sulfate is acetonitrile.

Accordingly, the present invention provides a process for the preparation of crystalline isavuconazonium sulfate comprising:

(a) providing a reaction mixture comprising isavuconazonium sulfate and a solvent system comprising of acetonitrile and water;

(b) stirring the reaction mixture of step (a) to precipitate isavuconazonium sulfate; and (c) isolating crystalline isavuconazonium sulfate, which is characterised by one or more data selected from the group consisting of an XRPD pattern having peaks at 6.45, 7.25, 15.98, 16.87, 17.25 and 20.93±0.2 degrees 2-theta; an IR spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±2 $cm^{-1}$; and a thermogravimetric analysis (TGA) thermogram, showing a weight loss of about 6.56% up to 150° C. determined over the temperature range of 0° C. to 250° C., and heating rate of 10° C./min.

In an embodiment, the present invention provides a process for the preparation of crystalline isavuconazonium sulfate comprising:

(A) providing an aqueous solution of isavuconazonium sulfate;

(B) adding a nitrile solvent as an anti-solvent to the aqueous solution of isavuconazonium sulfate of step (A) to precipitate isavuconazonium sulfate; and (C) isolating crystalline isavuconazonium sulfate as obtained in step (B) above.

The term "anti-solvent," as used herein, refers to a solvent in which a compound is insoluble at a given concentration for effectively precipitating the compound from a solution with that solvent.

In an embodiment, the nitrile solvent, which is used as an anti-solvent in the above step (B), is selected from the group consisting of acetonitrile, propionitrile and isobutyronitrile.

In an embodiment, the nitrile solvent, which is used as an anti-solvent is acetonitrile.

In an embodiment, the present invention provides a process for the preparation of crystalline isavuconazonium sulfate (Form GL-1) comprising treating isavuconazonium sulfate with a solvent system comprising acetonitrile and water, wherein the resulting crystalline isavuconazonium sulfate is characterized by an XRPD pattern having peaks at 6.45, 7.25, 15.98, 16.87, 17.25 and 20.93±0.2 degrees 2-theta. The resulting crystalline isavuconazonium sulfate (Form GL-1) is further characterized by an XRPD pattern having one or more additional peaks at 12.5, 17.83, 21.99 and 22.56±0.2 degrees 2-theta.

In an embodiment, the present invention provides a process for the preparation of crystalline isavuconazonium sulfate (Form GL-1) comprising treating isavuconazonium sulfate with a solvent system comprising acetonitrile and water, wherein the resulting crystalline isavuconazonium sulfate is characterized by an XRPD pattern having peaks at 6.45, 7.25, 12.5, 15.98, 16.87, 17.25, 17.83, 20.93, 21.99 and 22.56±0.2 degrees 2-theta.

In an embodiment, the present invention provides a process for the preparation of crystalline isavuconazonium sulfate (Form GL-1) comprising isolating crystalline isavuconazonium sulfate (Form GL-1) from a solvent system comprising a mixture of a nitrile solvent and water.

In an embodiment, the present invention provides a process for the preparation of crystalline isavuconazonium sulfate (Form GL-1) comprising isolating crystalline isavuconazonium sulfate from a solvent system comprising a mixture of acetonitrile and water.

In an embodiment, as may be combined with the preceding paragraphs, the present invention provides a process for the preparation of crystalline isavuconazonium sulfate (Form GL-1) wherein in step (a) of the process, the reaction mixture may be obtained by a process comprising:

(i) providing an aqueous solution of isavuconazonium sulfate;

(ii) passing the aqueous solution of isavuconazonium sulfate obtained in step '(i)' through a polyethersulfone-based nano filtration membrane (PES); and (iii) treating the solution obtained in step '(ii)' with a nitrile solvent to obtain the reaction mixture.

In an embodiment, in step (ii), the aqueous solution of step (i) is passed through a polyethersulfone-based nano filtration membrane (PES) to obtain an aqueous solution having a concentration of isavuconazonium sulfate of about 30% to about 50% of total volume.

In an embodiment, in step (ii), the polyethersulfone-based nano filtration membrane (PES) has a diameter of about 150 to about 300 Daltons.

In an embodiment, it was surprisingly found that crystalline isavuconazonium sulfate (Form GL-1) may be obtained without subjecting it to lyophilisation.

Isavuconazonium sulfate, the compound of Formula I structurally represented hereinabove, is a mixture of epimers, namely, Epimer I and Epimer II represented by the following structures.

Epimer I

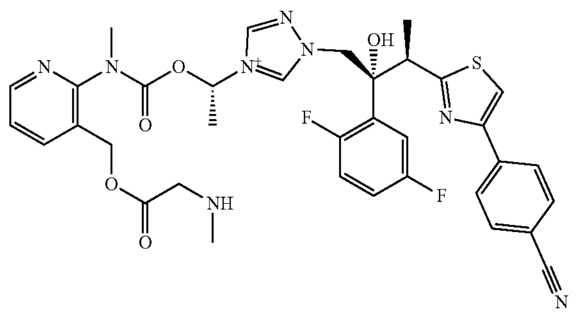

Epimer II

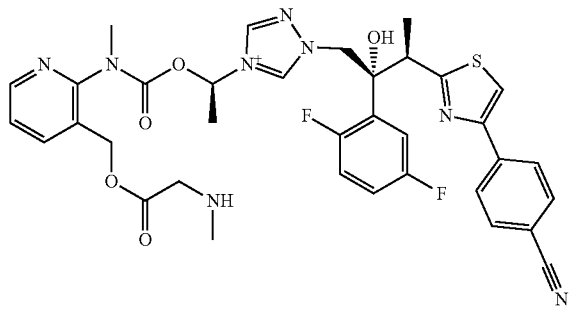

As used herein, the term "epimers" means diastereomers that differ from each other in stereochemistry at only one of many stereocenters.

In an embodiment, the present invention provides the crystalline isavuconazonium sulfate (Form GL-1) comprising Epimer I and Epimer II in a ratio of 1:1.

In the context of the present invention, a person of skill in the art will understand that a reference to crystalline isavuconazonium sulfate (Form GL-1) of the present invention also refers to crystalline isavuconazonium sulfate (Form GL-1) comprising Epimer I and Epimer II in a ratio of 1:1.

As discussed above, isavuconazonium sulfate is currently marketed in the form of capsules and injections under the trade name Cresemba®. This approved marketed product contains the amorphous form of isavuconazonium sulfate. (See, e.g., Ref.: Cresemba EPAR Public Assessment Report, EMA/596950/2015, 23 Jul. 2015).

It is found that the amorphous form of isavuconazonium sulfate is unstable, and generates impurities identified as the compounds of formulae IV, VI, VII, VIII, IX, X and XI represented below by their respective chemical structures.

IV

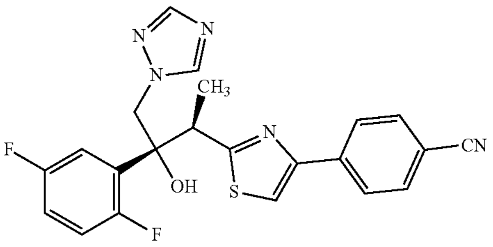

VI

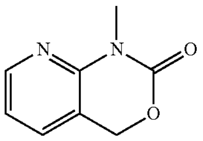

VII

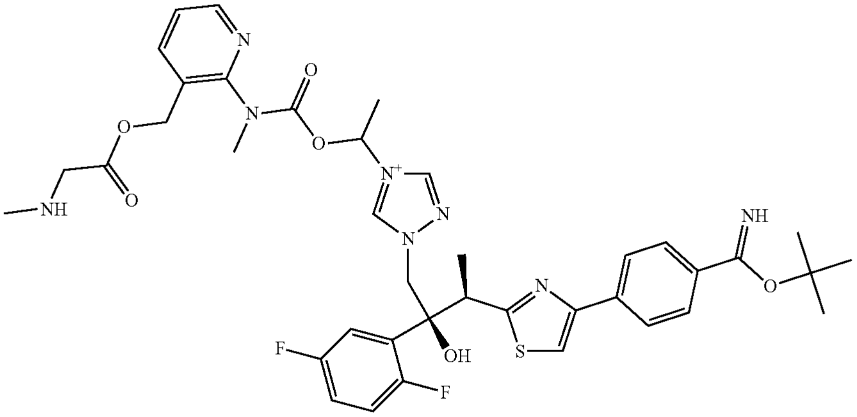

VIII

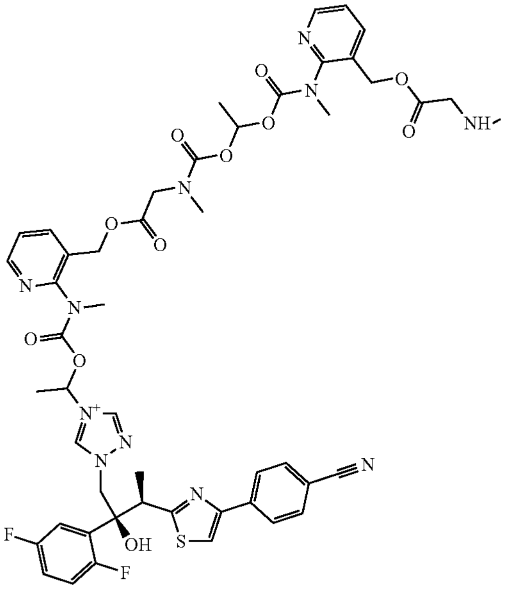

IX

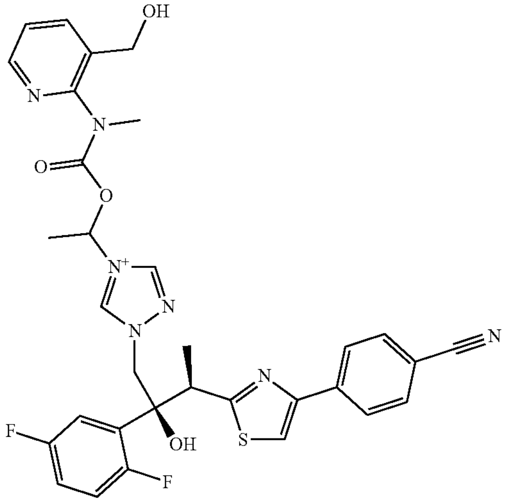

-continued

X

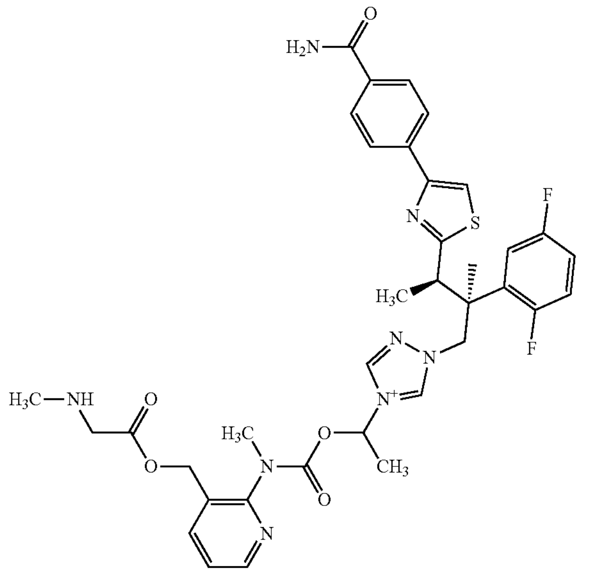

XI

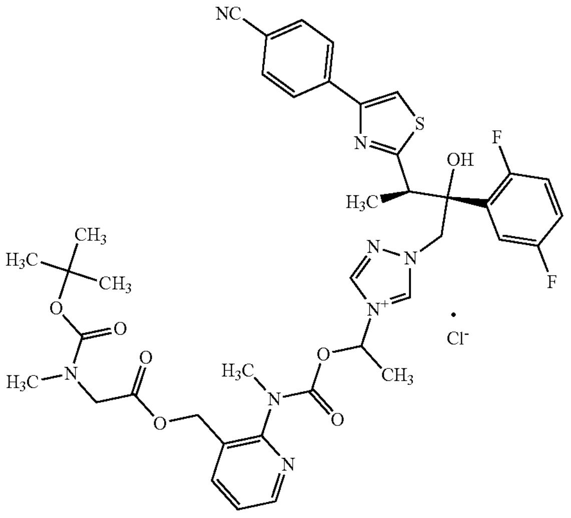

In generic drug development, it is very important to provide an active pharmaceutical ingredient (API) that exhibits a favourable impurity profile as safety of a drug is primarily dependent on the impurities that it contains. Therefore, it is desirable to have an API having a favourable impurity profile that provides an advantage in terms of ease of formulating the drug and improved storage stability. The crystalline isavuconazonium sulfate (Form GL-1) disclosed herein according to the non-limiting illustrative embodiments advantageously exhibits a favourable impurity profile while having an improved storage stability. In addition, the crystalline isavuconazonium sulfate (Form GL-1) disclosed herein can be obtained in a simple, cost efficient manner.

In an embodiment, the crystalline isavuconazonium sulfate (Form GL-1) as obtained in step (c) disclosed herein has a chemical purity of at least 90% as measured by high performance liquid chromatography (HPLC).

In an embodiment, the crystalline isavuconazonium sulfate (Form GL-1) as obtained in step (c) disclosed herein has a chemical purity of at least 99% as measured by HPLC.

In an embodiment, the crystalline isavuconazonium sulfate (Form GL-1) as obtained in step (c) disclosed herein has a chemical purity of at least 99.9% as measured by HPLC.

In an embodiment, the present invention provides crystalline isavuconazonium sulfate (Form GL-1), wherein the Form GL-1 contains an impurity selected from the compounds of formulae IV, VI, VII, VIII, IX, X or XI (as described above) in less than about 0.2% w/w. The contents of compounds of formulae IV, VI, VII, VIII, IX, X or XI are measured by HPLC.

Further, in an embodiment, the present invention provides a process for the preparation of crystalline isavuconazonium sulfate (Form GL-1), wherein the Form GL-1 contains an impurity selected from the compounds of formulae IV, VI, VII, VIII, IX, X or XI (as described above) in less than about 0.2% w/w.

In an embodiment, the present invention provides a process for the preparation of crystalline isavuconazonium sulfate (Form GL-1) wherein the content of compounds of formula IV, VI, VII, VIII, IX, X or XI (as described above) present in the resulting crystalline isavuconazonium sulfate (Form GL-1) is from about 0.03% to about 0.2% w/w as measured by HPLC.

Apart from favourable impurity profile of the API, it is equally important that the API exhibits substantial stability throughout the manufacturing of the drug product, and further, in the stages of packaging, storage, distribution and use of the drug product. In accordance with the non-limiting illustrative embodiments disclosed herein, the inventors of the present invention have been successful in providing the crystalline isavuconazonium sulfate (Form GL-1) that is substantially stable in comparison to the amorphous form contained in the marketed product, Cresemba, as will be apparent from the comparative stability data provided in the experimental section.

The term "stable", as used herein, refers to crystalline isavuconazonium sulfate (Form GL-1), which substantially retains its chemical purity, and does not degrade on storage. Under its accepted and customary meaning, the term "storage" in respect of a product means that the product maintains its stability during its shelf life for its intended use. As an example, a specific stability test to determine the chemical stability of crystalline isavuconazonium sulfate (Form GL-1) when stored at certain storage conditions is described in the experimental section.

Herein is described a stable crystalline isavuconazonium sulfate (Form GL-1) characterized by XRPD pattern having peaks at 6.45, 7.25, 15.98, 16.87, 17.25 and 20.93±0.2 degrees 2-theta, which does not have any detectable quantity of any of the impurities selected from the compounds of formulae IV, VI, VII, VIII, IX, X or XI. The stable crystalline isavuconazonium sulfate (Form GL-1) is further characterized by an XRPD pattern having one or more additional peaks at 12.5, 17.83, 21.99 and 22.56±0.2 degrees 2-theta.

In an embodiment, the present invention provides a process for the preparation of stable crystalline isavuconazonium sulfate (Form GL-1) which is characterized by an XRPD pattern having peaks at 6.45, 7.25, 15.98, 16.87, 17.25 and 20.93±0.2 degrees 2-theta, which does not have any detectable quantity of any of the impurities selected from the compounds of formulae IV, VI, VII, VIII, IX, X, or XI.

The term “detectable quantity” as used herein refers to an amount of the above-mentioned compounds of formulae IV, VI, VII, VIII, IX, X, or XI determined using an analytical method, which can detect each of the above specified impurity in an amount greater than 0.03% w/w. Accordingly, the term “not detectable quantity” indicates the amount in which any of the impurities selected from the compounds of formulae IV, VI, VII, VIII, IX, X, or XI is less than 0.03% w/w or are absent.

In an illustrative embodiment, a stability study was performed on crystalline isavuconazonium sulfate (Form GL-1) of the present invention as per the method described in the experimental section. The stability study data presented in the experimental section confirms that the crystalline isavuconazonium sulfate (Form GL-1) of the present invention and as described herein is stable at 3 months under the storage conditions specified herein.

Accordingly, in an embodiment, the present invention provides stable crystalline isavuconazonium sulfate (Form GL-1) having a content of any of the impurities selected from the compounds of formulae IV, VI, VII, VIII, IX, X or XI less than about 0.2% w/w as determined by HPLC.

In an embodiment, the present invention provides stable crystalline isavuconazonium sulfate (Form GL-1) having a content of any of the impurities selected from the compounds of formulae IV, VI, VII, VIII, IX, X or XI in an amount from about 0.03% to about 0.2% w/w as determined by HPLC.

Accordingly, in an embodiment, the present invention provides stable crystalline isavuconazonium sulfate (Form GL-1) having a content of any of the impurities selected from the compounds of formulae IV, VI, VII, VIII, IX, X or XI in an amount from about 0.03% to about 0.2% w/w as determined by HPLC at 3 months under the storage conditions specified herein.

The term “about” used in reference to the content of impurities refers to a range which is typically within 1%, more typically within 0.5% of the indicated value or range. The allowable variation encompassed by the term “about” depends on the system under study and that which can be appreciated by a person skilled in the art.

Isavuconazonium sulfate used in step (a) of the process for the preparation of crystalline isavuconazonium sulfate (Form GL-1) of the present invention as disclosed herein, may be prepared by following a process disclosed in IN201821035971 wherein the process comprises:

(i) reacting a compound of formula II,

II

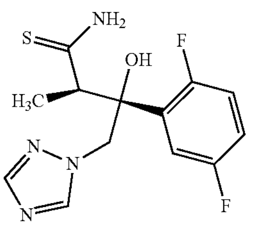

with a compound of formula III,

III

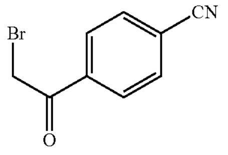

in the presence of methanol to obtain a reaction mixture containing isavuconazole, a compound of formula IV;

IV

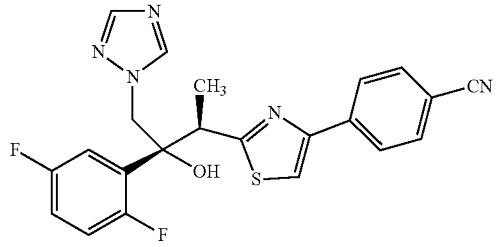

(j) reacting isavuconazole, the compound of formula IV obtained from the above reaction mixture with a compound of formula V,

V

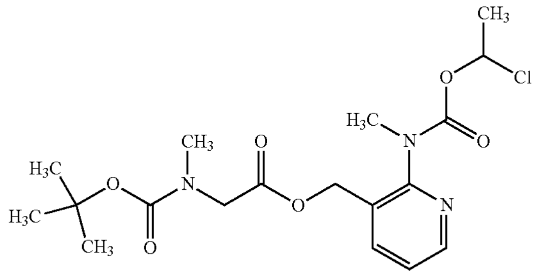

in the presence of an iodide source to obtain N-Boc isavuconazonium iodide;

k) converting the N-Boc isavuconazonium iodide to N-Boc isavuconazonium chloride, a compound of formula XI; and l) converting the N-Boc isavuconazonium chloride to isavuconazonium sulfate.

The present invention also provides a pharmaceutical composition comprising crystalline isavuconazonium sulfate (Form GL-1) and at least one pharmaceutically acceptable excipient.

The pharmaceutical composition of the present invention may be orally administered to a subject in need thereof, in the dosage form of, for example, a tablet, capsule, granule or powder, or parenterally administered in the form of injection, or intranasally, or in the form of transdermal patch.

In an embodiment, the pharmaceutical composition of the present invention may be orally administered to a subject in need thereof, in the dosage form selected from a tablet or a capsule.

In another embodiment, the pharmaceutical composition of the present invention may be parenterally administered, in the form of injection to a subject in need thereof.

In an illustrative embodiment, the pharmaceutical composition comprises the crystalline isavuconazonium sulfate (Form GL-1) described herein in a therapeutically effective amount. The term “therapeutically effective amount” as used herein means the amount of a compound that, when administered to a mammal for treating a state, disorder or condition, is sufficient to effect such treatment. The “therapeutically effective amount” will vary depending on the compound, the disease and its severity and the age, weight, physical condition and responsiveness of the mammal to be treated.

The term “administering” as used herein means providing a therapeutically effective amount of an active ingredient to a particular location within a subject means causing a therapeutically effective blood concentration of the active ingredient at the particular location. This can be accomplished, e.g., by topical, oral, local or by systemic administration of the active ingredient to the subject.

The term “pharmaceutically acceptable excipient” as used herein refers to substances, which do not show a significant therapeutic or pharmacological activity at a particular dose of the drug, and that are added to a pharmaceutical composition in addition to the active pharmaceutical ingredient (API).

The pharmaceutically acceptable excipient that is used in the pharmaceutical composition of the present invention, may be selected from the group consisting of carriers, fillers, diluents, lubricants, sweeteners, stabilizing agents, solubilizing agents, antioxidants and preservatives, flavouring agents, binders, colorants, osmotic agents, buffers, surfactants, disintegrants, granulating agents, coating materials and combinations thereof.

As mentioned above, isavuconazonium sulfate is marketed under the tradename CRESEMBA® as capsules containing 186 mg of isavuconazonium sulfate, and also, as powder for IV (Infusion) containing 372 mg of isavuconazonium sulfate.

Accordingly, it can be easily understood by a person skilled in the art to formulate crystalline isavuconazonium sulfate of the present invention into a suitable dosage form according to dose of the drug to be administered.

In another embodiment, the present invention also relates to a method for the treatment of fungal infections comprising administering a therapeutically effective amount of crystalline isavuconazonium sulfate (Form GL-1) disclosed herein to a subject in need thereof.

As used herein the term “a subject in need thereof” is a mammal having a fungal infection, or a mammal at risk of developing a fungal infection. The subject may have been diagnosed as having such a fungal infection as described herein. Alternatively, a subject may exhibit one or more symptoms of fungal infection.

The term “subject” or “a patient” as used herein refers to mammalian animals, preferably a human.

The fungal infections may be topical and mucosal fungal infections caused by, among other genera, Candida, Trichophyton, or Microsporum.

In an embodiment, the crystalline isavuconazonium sulfate (Form GL-1) of the present invention or the pharmaceutical composition comprising the said crystalline isavuconazonium sulfate (Form GL-1) as disclosed herein is provided for use in the treatment of fungal infections selected from mucormycosis or invasive aspergillosis.

The examples that follow are provided to enable one skilled in the art to practice the invention, and are merely illustrative of the invention. The examples should not be read as limiting the scope of the invention.

EXAMPLES

General Methods:

1. HPLC Method:

High performance liquid chromatography (HPLC) was performed with the conditions described below for detecting chemical purity:

Column: Xterra MS C18, 150×4.6 mm, 3.5μ; Column Temperature: 45° C., Mobile phase: Mobile Phase A; 0.1% Perchloric acid in water: Mobile Phase B=Methanol

| Time (min) | % Mobile Phase A | % Mobile Phase B |
|---|---|---|
| 0.01 | 70 | 30 |
| 03 | 70 | 30 |
| 30 | 40 | 60 |
| 42 | 20 | 80 |
| 60 | 20 | 80 |
| 62 | 70 | 30 |
| 70 | 70 | 30 |

Diluent: Methanol: 0.3% Sodium bisulphate (70:30 v/v); Flow Rate: 1.0 mL/Minutes, Detection: 260 nm; Injection Volume: 20 μL.

2. Infrared Spectrophotometry (Instrumental Settings):

Instrument Name: Perkin Elmer; Model: Spectrum 1; Method: 300-400 mg of KBr, previously dried at 200° C. and cooled was taken into a mortar and ground to a fine powder. 1.0 mg-2.0 mg of test sample, was added and mixed well and ground to a fine powder. A small quantity of powder was taken and a thin semi-transparent pellet was made from the powder. The IR spectrum of the pellet was recorded from 4000 $cm^{-1}$ to 650 $cm^{-1}$ taking air as a reference.

3. X-Ray Powder Diffraction (XRPD) (Instrumental Settings):

The measurements were performed on Philips X-Ray Diffractometer model XPERT-PRO (PANalytical) Detector: X’celerator [1] using Cu lamp with type and wavelength of the X-ray radiation: K-$\alpha_1$ 1.54060 [Å], K-$\alpha_2$ 1.5444 [Å] under the following conditions: The measurements were carried out with a Pre FIX module programmable divergence slit and anti-scatter Slit (Offset 0.00°); Generator settings: 40 mA/45 kV, tube current 40 mAmp Time per step: 50 s, Step size: 0.0167, Peak width 2.00 and start angle (°) 2.0 and End angle: 50.0; Scan type: continuous; measurement performed at 25° C. The XRPD instrument is calibrated using NIST SRM 6-40C silicon standard and NIST SRM 1976 Alumina.

Sample preparation: Take an adequate amount of the sample to fill the sample holder using back-loading technique. Then load the sample holder between the X-ray optics-path and scan using the above described parameters. Integrate the obtained powder X-ray diffraction profiles using X’Pert HighScore Plus Software.

4. Thermogravimetric Analysis (Instrumental Settings):

TGA thermogram was recorded using TGA-Q500 (Waters). About 5-10 mg of sample was taken in sample holder and loaded it in furnace. The sample was heated up to 250° C. at the ramp rate of 10° C./min and the thermogram was integrated by using Universal V4.5A software.

5. Percentage Crystallinity (Instrumental Settings):

The percentage crystallinity analysis was carried out by inserting the measurement file xrdml (X-ray powder diffraction measurement data) in X’pert HighScore Plus software. The manual ranges are set for the start position [°2θ] and clipped. The high granularity and “0” bending factor was selected through automatic background measurement. The process was repeated and the background defined so that the amorphous hump is taken into background. The minimum intensity from scattering value was used as an input for the constant background in the scan statistics. The crystallinity [%] value was then calculated.

PANalytical Highscore uses crystallinity algorithm as, $$\text{Crystallinity [\%]} = 100\times\sum Inet./\left(\sum Itotal.-\sum I \text{ constant background}\right);$$

wherein "Inet" refers to area of the crystalline peaks, "Itotal" refers to the combined area of crystalline and amorphous peaks, and "Iconstant background" refers to the amorphous area in the diffractogram.

EXAMPLES

Example 1

Synthesis of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy) carbonyl](methyl)amino}pyridin-3-yl)methyl-N-methylglycinate monosulfate salt (Isavuconazonium Sulfate)

4H-1,2,4-triazolium, 1-[(2R,3R)-3-[4-(4-cyanophenyl)-2-thiazolyl]-2-(2,5-difluorophenyl)-2-hydroxybutyl]-4-[1-[[[[3-[[[2-[[(1,1-dimethylethoxy)carbonyl]methylamino] acetyl]oxy]methyl]-2-pyridinyl]methylamino]carbonyl] oxy]ethyl]chloride (compound XI, 125 gm) was suspended in isopropyl acetate (1875 mL). The reaction mass was cooled to 10° C. to 20° C. and to this 8-12% of hydrochloric acid (625 mL) in ethyl acetate was added. The reaction mixture was stirred at 10-20° C. for 3 hours. On completion of the reaction, celite was added and stirred for 10 minutes. The product was filtered and washed with ethyl acetate. To the wet cake, water and methylene dichloride was added, stirred and filtered. The aqueous layer was passed through sulfate containing anion exchange resin. The aqueous solution containing isavuconazonium sulfate from the resin column was distilled under vacuum below 30° C. to obtain oily residue. Purity: 94.53%. Acetonitrile (2500 mL) and water (62.5 mL) was added to the residue and stirred for 12 hr. The precipitated product was filtered to obtain (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy)carbonyl](methyl)amino}pyridin-3-yl)methyl-N-methylglycinate monosulfate salt.

Purity: 99.5%, as measured by the HPLC method described above. The content of each of the impurities of the compounds of formulae IV, VI, VII, VIII, IX, X and XI as measured by HPLC is less than 0.2% w/w.

Example—2

Synthesis of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy) carbonyl](methyl)amino}pyridin-3-yl)methyl-N-methylglycinate monosulfate salt (Isavuconazonium Sulfate)

4H-1,2,4-triazolium, 1-[(2R,3R)-3-[4-(4-cyanophenyl)-2-thiazolyl]-2-(2,5-difluorophenyl)-2-hydroxybutyl]-4-[1-[[[[3-[[[2-[[(1,1-dimethylethoxy)carbonyl]methylamino] acetyl]oxy]methyl]-2-pyridinyl]methylamino]carbonyl] oxy]ethyl]chloride (compound XI, 10 gm) was suspended in isopropyl acetate (150 ml). The reaction mass was cooled to 10° C. to 20° C. and to this 8 to 12% of hydrochloric acid (50 mL) in ethyl acetate was added. The reaction mass stirred at 10-20° C. for 3 hr. On completion, celite was added and stirred for 10 min. The product was filtered and washed with ethyl acetate. Water and methylene dichloride was added to the wet cake, stirred and filtered. The aqueous layer was passed through a sulfate containing anion exchange resin with water wash. The aqueous solution from the sulfate containing anion exchange resin was passed through a polyethersulfone-based nano filtration membrane (PES) having a diameter of 150-300 Daltons to achieve concentration of an aqueous layer above 35%. Purity of the aqueous layer was 96.5%. To the aqueous layer acetonitrile (200 mL) was added and stirred for 12 hr. The precipitated product was filtered to get (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy)carbonyl](methyl) amino}pyridin-3-yl)methyl-N-methylglycinate sulfonium salt (5 gm).

Purity: >99%, as measured by the HPLC method described above. The content of each of the impurities of the compounds of formulae IV, VI, VII, VIII, IX, X and XI as measured by HPLC is less than 0.2% w/w.

Example—3

Synthesis of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy) carbonyl](methyl)amino}pyridin-3-yl)methyl-N-methylglycinate monosulfate salt (Isavuconazonium Sulfate)

4H-1,2,4-triazolium, 1-[(2R,3R)-3-[4-(4-cyanophenyl)-2-thiazolyl]-2-(2,5-difluorophenyl)-2-hydroxybutyl]-4-[1-[[[[3-[[[2-[[(1,1-dimethylethoxy)carbonyl]methylamino] acetyl]oxy]methyl]-2-pyridinyl]methylamino]carbonyl] oxy]ethyl]chloride (compound XI, 400 gm) was suspended in water (2000 mL) and Conc. HCl (366 gm) solution. The reaction mixture was stirred at 20-30° C. for 12 hr. To the reaction mixture, methylene dichloride (4000 mL) was added, stirred. The layers were separated. The product containing aqueous layer was passed through sulfate containing anion exchange resin. The aqueous solution from sulfate containing anion exchange resin was passed through Nano filtration Polyether sulfone (PES) having a diameter of 150-300 (Dalton). The water content was reduced till it remained to about 1 to 2 volumes of retentate and to this acetonitrile (25 volume) was added with respect to the retentate volume and stirred for 5 to 6 hr. The precipitated product was filtered, and dried to obtain 172 gm of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy)carbonyl](methyl)amino}pyridin-3-yl)methyl-N-methylglycinate sulfonium salt. Purity: 99.76%, as measured by the HPLC method described above. The content of each of the impurities of the compounds of formulae IV, VI, VII, VIII, IX, X and XI as measured by HPLC is less than 0.2% w/w.

The crystalline isavuconazonium sulfate obtained as per example 3 was analysed by powder X-ray diffraction, IR spectroscopy and TG study. The results are depicted in FIGS. 1, 2 and 3 respectively.

Example 4

Synthesis of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy) carbonyl](methyl)amino}pyridin-3-yl)methyl-N-(tert-butoxycarbonyl)-N-methylglycinate chloride (Compound XI)

4-{2-[(2R,3R)-3-(2,5-difluorophenyl)-3-hydroxy-4-(1H-1,2,4-triazol-1-yl)butan-2-yl]-1,3-thiazol-4-yl}benzonitrile (compound IV, 880 gm) was suspended in a mixture of methyl isobutyl ketone (3520 mL) acetonitrile (1760 mL) to obtain a reaction mass. To this reaction mass was added (2-{[(1-chloroethoxy)carbonyl](methyl)amino}pyridin-3-yl)methyl-N-(tert-butoxycarbonyl)-N-methylglycinate (compound V, 1086 g) and sodium iodide (361.7 g). The reaction mass was heated to a temperature 35° C. to 45° C. and maintained for about 8-9 hours at a temperature from about 35° C. to 45° C. The reaction mass was filtered and the filtrate was distilled under vacuum. The obtained residue was dissolved in methanol (7920 ml) and added 7920 ml of SA10A (chloride) resin and reaction mass stirred for a period of about 1.0 hr. The reaction mass was filtered and washed with methanol. To the filtrate chloride resin (5280 mL) was added and stirred for a period of about 1 hour and filtered. To the filtrate added water and toluene were added. The layers were separated and the aqueous layer was washed with toluene followed by extraction of the aqueous layer with methylene dichloride (MDC). Then MDC layer was washed with 2% hydrochloric acid solution and 10% sodium chloride solution and then the MDC layer was distilled and the residue obtained was dissolved in ethyl acetate (2640 ml) and this solution was added in to pre chilled n-heptane (7040 mL) at −5 to 5° C. The precipitated product was filtered and dried at 45-50° C. under vacuum to obtained 1188 g of title product. Purity: 98.91%, as measured by the HPLC method described above.

Example 5

Stability Study of Crystalline Isavuconazonium Sulfate:

Comparative stability data was generated for crystalline isavuconazonium sulfate (Form GL-1) and the amorphous form of isavuconazonium sulfate (prepared as described in Comparative Example 1) stored at a temperature of −20° C. and from 2° to 8° C. for three (3) months (i.e., 12 weeks). In particular, the crystalline isavuconazonium sulfate (Form GL-1) obtained as per Example 3 and the amorphous form of isavuconazonium sulfate of Comparative Example 1 were taken in an appropriate amount, and packed in a transparent polyethylene bag. The bag was sealed under vacuum and then enclosed in a black LDPE (Low-density polyethylene) bag which in turn is kept in triple laminated aluminium pouches sealed at three sides. The fourth side of the bag is then sealed under vacuum and kept in a HDPE (High-density polyethylene) container, and stored at −20° C. and from 2° to 8° C. for 3 months (i.e., 12 weeks). Both materials were analyzed after 3 months of storage by the HPLC method described above.

The stability data of the crystalline isavuconazonium sulfate (Form GL-1) in comparison to the amorphous isavuconazonium sulfate is presented in the following Table 1.

TABLE 1

| Isavuconazonium sulfate Polymorph | Impurity (Compound) | Time Period: Initial | 3 Month at −20° C. | 3 Month at 2°-8° C. |
|---|---|---|---|---|
| Crystalline isavuconazonium sulfate (Form GL-1) of Example 3 | Compound IV | 0.03% | 0.05% | 0.07% |
| | Compound VI | 0.01% | 0.02% | 0.03% |
| | Compound VII | 0.08% | 0.08% | 0.08% |
| | Compound VIII | 0.03% | 0.03% | 0.02% |
| | Compound IX | 0.09% | 0.09% | 0.13% |
| | Compound X | 0.05% | 0.08% | 0.07% |
| | Compound XI | ND | ND | ND |
| Amorphous isavuconazonium sulfate prepared as per comparative example 1 | Compound IV | 0.21% | 0.41% | 0.76% |
| | Compound VI | 0.04% | 0.10% | 0.33% |
| | Compound VII | 0.12% | 0.12% | 0.12% |
| | Compound VIII | 0.44% | 0.44% | 0.44% |
| | Compound X | 0.03% | 0.03% | 0.04% |
| | Compound IX | 0.51% | 1.26% | 2.5% |
| | Compound XI | ND | ND | ND |

In the above table, ND—Not detected

The stability data presented in the above Table 1 demonstrates that the stability of the crystalline isavuconazonium sulfate (Form GL-1) is maintained at least up to three (3) months when stored under the storage condition as specified above. Form GL-1 is found to be more stable compared to the amorphous form of isavuconazonium sulfate over the period of 3 months.

Reference Example 1

Synthesis of 4-{2-[(2R,3R)-3-(2,5-difluorophenyl)-3-hydroxy-4-(1H-1,2,4-triazol-1-yl)butan-2-yl]-1,3-thiazol-4-yl}benzonitrile (Compound IV)

To (2R,3R)-3-(2,5-difluorophenyl)-3-hydroxy-2-methyl-4-(1H-1,2,4-triazol-1-yl)butane-thioamide (compound II, 50 gm) in isopropyl alcohol (II, 150 mL) was added 4-(bromoacetyl)benzonitrile (compound III, 35.9 gm) to obtain a reaction mass. The reaction mass was heated to 40-50° C. On completion of the reaction, the solvent was distilled, and ethyl acetate and water were added to the reaction mass. The pH of reaction mass was adjusted by aqueous solution of sodium bicarbonate to 7.0-8.0. The layers were separated and the organic layer was washed with saturated sodium chloride solution. The organic layer was distilled to get oily mass. To the oily mass isopropyl alcohol was added and the solution was heated at a temperature from 55° C. to 65° C. followed by addition of water. The reaction mass was cooled to 15° C. to 25° C. and stirred for 4 hours. The solid obtained was filtered and washed with a mixture of isopropyl alcohol and water to get 4-{2-[(2R,3R)-3-(2,5-difluorophenyl)-3-hydroxy-4-(1H-1,2,4-triazol-1-yl)butan-2-yl]-1,3-thiazol-4-yl}benzonitrile (54 gm) purity by HPLC: 99.96%.

Reference Example 2

Synthesis of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy) carbonyl]-(methyl)amino}pyridin-3-yl)methyl-N-(tert-butoxycarbonyl)-N-methylglycinate chloride (Compound XI)

4-{2-[(2R,3R)-3-(2,5-difluorophenyl)-3-hydroxy-4-(1H-1,2,4-triazol-1-yl) butan-2-yl]-1,3-thiazol-4-yl}benzonitrile (compound IV, 100 g) of Reference example 1 was suspended in acetonitrile (750 mL) followed by addition of (2-{[(1-chloroethoxy)carbonyl](methyl)amino}pyridin-3-yl)methyl-N-(tert-butoxycarbonyl)-N-methyl-glycinate (compound V, 128 gm) to obtain a reaction mass. The reaction mass was heated at a temperature from 55° C. to 60° C. A solution of sodium iodide (41.11 gm) in acetonitrile (650 mL) was added and the reaction mass was maintained for about 8-10 hours at a temperature of about 55° C. to 60° C. The reaction mass was filtered and the filtrate was distilled completely under vacuum. The obtained residue was dissolved in methanol (600 mL) and added Diaion®SA10A (chloride) (900 mL) resin and reaction mass stir for 1 hour. The reaction mass was filtered and washed with methanol to isolate resulting product. Purity by HPLC: 89.56%.

To the above obtained solution water and toluene were added. The layers were separated and the aqueous layer was washed with toluene followed by extraction of the aqueous layer with methylene dichloride (MDC). The MDC layer was distilled and residue was dissolved in ethyl acetate (400 mL) and to this n-heptane (1000 mL) was added. The product was precipitated at a temperature from −5° C. to 0° C. was filtered and dried at temperature of 45-50° C. under vacuum to obtain 130 g of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy)carbonyl](methyl)amino}pyridin-3-yl)methyl-N-(tert-butoxycarbonyl)-N-methylglycinate chloride. Purity by HPLC: 97.81%.

Comparative Example 1

Synthesis of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy) carbonyl](methyl)amino}pyridin-3-yl)methyl-N-methylglycinate monosulfate salt (Amorphous Form)

4H-1,2,4-triazolium, 1-[(2R,3R)-3-[4-(4-cyanophenyl)-2-thiazolyl]-2-(2,5-difluorophenyl)-2-hydroxybutyl]-4-[1-[[[[3-[[[2-[[(1,1-dimethylethoxy)carbonyl]methylamino] acetyl]oxy]methyl]-2-pyridinyl]methylamino]carbonyl] oxy]ethyl]chloride (120 gm) was suspended in isopropyl acetate (compound XI, 1800 mL). The reaction mass was cooled to 10° C. to 20° C. and to this 8-12% of hydrochloric acid (600 mL) in ethyl acetate was added. The reaction mixture was stirred at 10-20° C. for 3 hours. On completion of the reaction, the product was filtered and washed with ethyl acetate. The wet cake dissolved in 360 mL of water and the aqueous layer was washed with methylene dichloride. The aqueous layer was passed through a sulfate containing anion exchange resin. The aqueous solution containing isavuconazonium sulfate from the resin column was washed with 10% n-Butanol-methylene dichloride (1200 mL). The obtained aqueous layer was washed with methylene dichloride and cyclohexane. Then aqueous layer is then lyophilized at a temperature of −80° C. to obtain 68 gm of the amorphous form of (2-{[(1-{1-[(2R,3R)-3-[4-(4-cyanophenyl)-1,3-thiazol-2-yl]-2-(2,5-difluorophenyl)-2-hydroxybutyl]-1H-1,2,4-triazol-4-ium-4-yl}ethoxy)carbonyl] (methyl)amino}pyridin-3-yl)methyl-N-methylglycinate monosulfate salt. purity 97.29%.

The invention claimed is:

1. A crystalline form of isavuconazonium sulfate (Form GL-1) characterized by an X-ray powder diffraction (XRPD) pattern having peaks at 6.45, 7.25, 15.98, 16.87, 17.25 and 20.93±0.2 degrees 2-theta.

2. The crystalline form of isavuconazonium sulfate (Form GL-1) according to claim 1, wherein the crystalline form is further characterized by the XRPD pattern having one or more additional peaks at 12.5, 17.83, 21.99 and 22.56±0.2 degrees 2-theta.

3. A crystalline form of isavuconazonium sulfate (Form GL-1) characterized by an X-ray powder diffraction (XRPD) pattern substantially as shown in FIG. 1.

4. The crystalline form of isavuconazonium sulfate (Form GL-1) according to claim 1, wherein the crystalline form is further characterized by an IR spectrum as shown in FIG. 2.

5. The crystalline form of isavuconazonium sulfate (Form GL-1) according to claim 1, wherein the crystalline form is further characterized by a TGA thermogram substantially as shown in FIG. 3.

6. The crystalline form of isavuconazonium sulfate (Form GL-1) according to claim 1, wherein the crystalline form comprises Epimer I and Epimer II represented by the following structures in a ratio of 1:1;

Epimer I

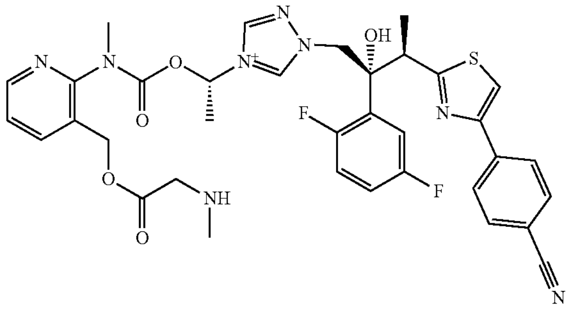

Epimer II

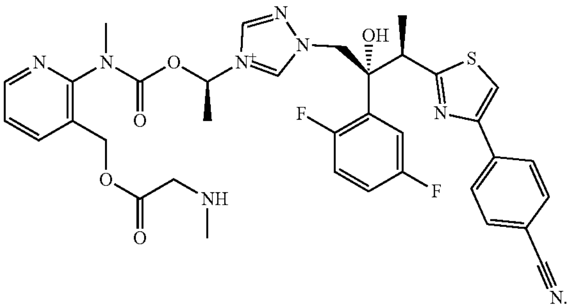

7. The crystalline form of isavuconazonium sulfate (Form GL-1) according to claim 1, wherein the crystalline form contains an impurity selected from the compounds of formulae IV, VI, VII, VIII, IX, X or XI represented below by their chemical structures:

IV
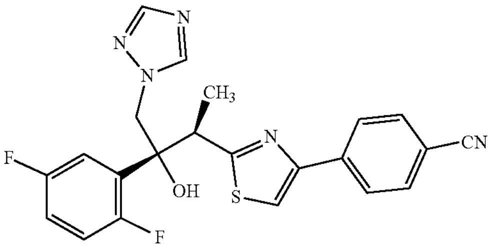
VI
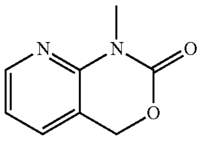
VII
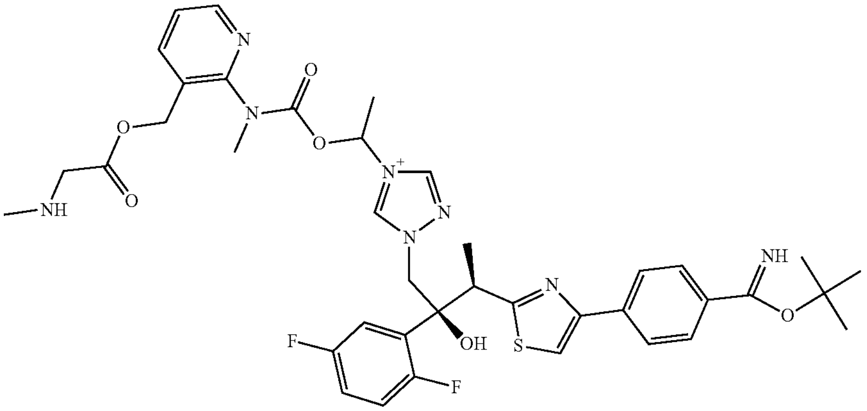
VIII
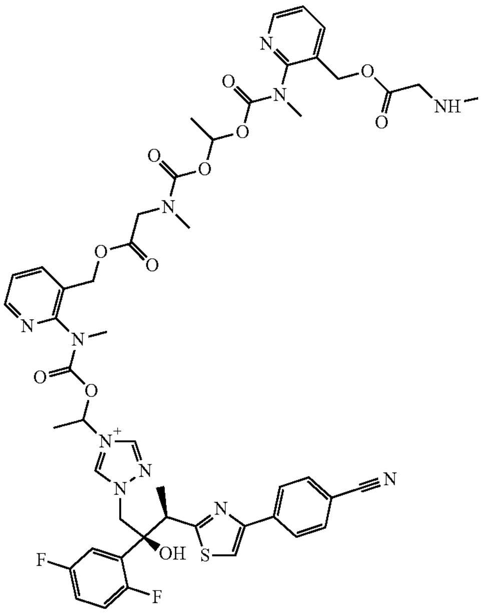
IX
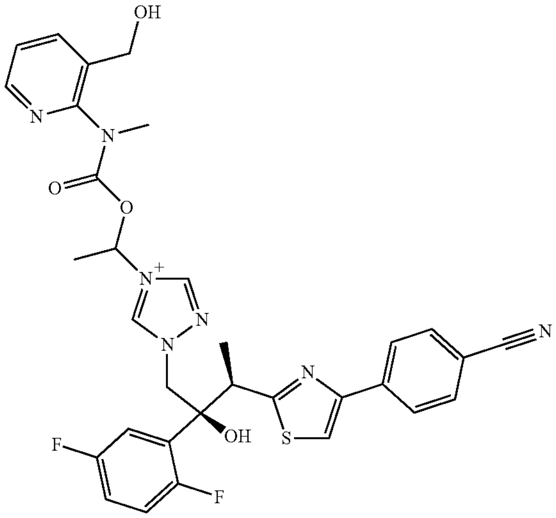

-continued

X

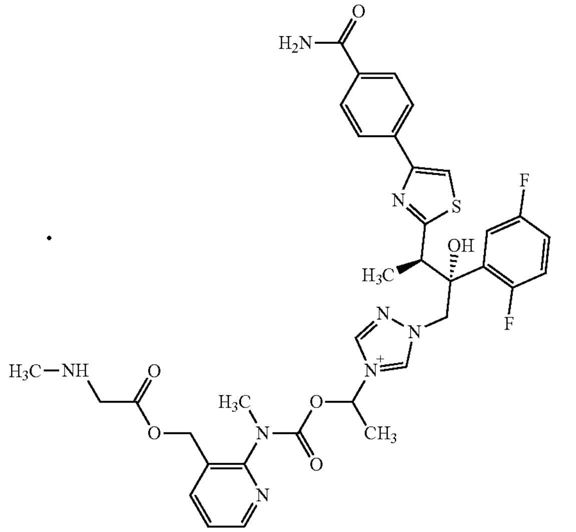

XI

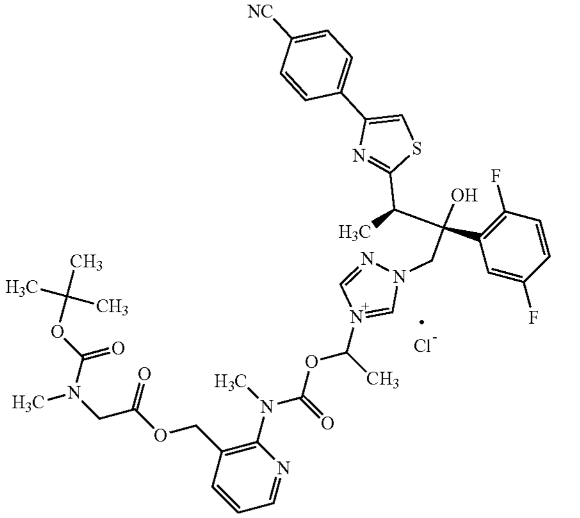

in an amount less than about 0.2% w/w.

8. A process for the preparation of a crystalline form of isavuconazonium sulfate (Form GL-1), comprising:

(a) providing a reaction mixture comprising isavuconazonium sulfate and a solvent system comprising a nitrile solvent and water;

(b) stirring the reaction mixture of step (a) to precipitate isavuconazonium sulfate; and (c) isolating isavuconazonium sulfate as obtained in step (b) in a crystalline form (Form GL-1);

wherein the crystalline form of isavuconazonium sulfate (Form GL-1) is characterized by an X-ray powder diffraction (XRPD) pattern having peaks at 6.45, 7.25, 15.98, 16.87, 17.25 and 20.93±0.2 degrees 2-theta.

9. The process according to claim 8, wherein the nitrile solvent is selected from the group consisting of acetonitrile, propionitrile and isobutyronitrile.

10. The process according to claim 9, wherein the nitrile solvent is acetonitrile.

11. The process according to claim 8, wherein the step (a) is carried out at a temperature of about 0° C. to about 25° C.

12. A method for the treatment of fungal infections, comprising:

administering a therapeutically effective amount of a crystalline form of isavuconazonium sulfate (Form GL-1) to a subject in need thereof, wherein the fungal infection is mucormycosis or invasive aspergillosis;

wherein the crystalline form of isavuconazonium sulfate (Form GL-1) is characterized by an X-ray powder diffraction (XRPD) pattern having peaks at 6.45, 7.25, 15.98, 16.87, 17.25 and 20.93±0.2 degrees 2-theta.

13. The crystalline form of isavuconazonium sulfate (Form GL-1) according to claim 1, wherein the crystalline form is further characterized by an IR (infra-red) spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±λ $cm^{-1}$; or a thermogravimetric Analysis (TGA) thermogram showing a weight loss of about 6.56% up to 150° C. determined over a temperature range of 0° C. to 250° C., and a heating rate of 10° C./min, or both.

14. The process according to claim 8, wherein the crystalline form is further characterized by an IR (infra-red) spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±λ $cm^{-1}$; or a thermogravimetric Analysis (TGA) thermogram showing a weight loss of about 6.56% up to 150° C. determined over a temperature range of 0° C. to 250° C., and a heating rate of 10° C./min, or both.

15. The method according to claim 12, wherein the crystalline form is further characterized by an IR (infra-red) spectrum having main bands at about 3412.33, 2432.59, 1756, 1578.51, 1447.24, 1379.27, 1325.65, 1305, 1216.36, 1116.29, 1063.94, 926.77, 894.63, 847.74, 819.96, 765.38 and 696.25±2 $cm^{-1}$; or a thermogravimetric Analysis (TGA) thermogram showing a weight loss of about 6.56% up to 150° C. determined over a temperature range of 0° C. to 250° C., and a heating rate of 10° C./min, or both.

* * * * *